(12) United States Patent
O'Hara et al.

(10) Patent No.: US 12,121,224 B2
(45) Date of Patent: Oct. 22, 2024

(54) LARYNGEAL STROBOSCOPE UTILIZING SOLID STATE LIGHT SOURCES

(71) Applicant: PENTAX of America, Inc., Montvale, NJ (US)

(72) Inventors: Vince O'Hara, Highland Lakes, NJ (US); Alind Sahay, West Chester, PA (US); Mohammad Elwakil, Seacaucus, NJ (US)

(73) Assignee: PENTAX OF AMERICA, INC., Montvale, NJ (US)

( * ) Notice: Subject to any disclaimer, the term of this patent is extended or adjusted under 35 U.S.C. 154(b) by 0 days.

(21) Appl. No.: 17/713,602

(22) Filed: Apr. 5, 2022

(65) Prior Publication Data

US 2022/0322925 A1  Oct. 13, 2022

Related U.S. Application Data

(60) Provisional application No. 63/171,666, filed on Apr. 7, 2021.

(51) Int. Cl.
*A61B 1/267* (2006.01)
*A61B 1/00* (2006.01)
(Continued)

(52) U.S. Cl.
CPC ...... *A61B 1/2673* (2013.01); *A61B 1/000095* (2022.02); *A61B 1/045* (2013.01);
(Continued)

(58) Field of Classification Search
CPC ....... A61B 1/2673; A61B 1/05; A61B 1/0676; A61B 1/0684; A61B 1/267; A61B 1/2676; A61B 1/063; A61B 1/0655; A61B 1/0661
See application file for complete search history.

(56) References Cited

U.S. PATENT DOCUMENTS 4,192,597 A   3/1980  Ting
4,297,017 A  10/1981  Farmer
(Continued)

FOREIGN PATENT DOCUMENTS

DE   102011007530 A1   10/2012
JP      2002306410 A   10/2002
(Continued)

OTHER PUBLICATIONS

Deguchi et al., "Preliminary Evaluation of Stroboscopy System Using Multiple Light Sources for Observation of Pathological Vocal Fold Oscillatory Pattern", Annals of Otology, Rhinology & Laryngology, vol. 116, No. 9, Sep. 2007, pp. 687-694.
(Continued)

*Primary Examiner* — Eduardo C Robert
*Assistant Examiner* — Angel Roberto Mora-Velazquez
(74) *Attorney, Agent, or Firm* — Kilpatrick Townsend & Stockton LLP

(57) ABSTRACT

Stroboscopic endoscopic systems and related methods employ intermittent energization of one or more light sources to generate a sequence of light flashes. A stroboscopic endoscope system includes an endoscope, an imaging device, a light source, a light transmission assembly, and a controller. The imaging device is configured for imaging an object illuminated via the endoscope. The light transmission assembly is configured to transmit light generated by the light source to the endoscope. The stroboscopic endoscopic systems and related methods employ approaches for increasing the amount of illumination light emitted by the endoscope.

14 Claims, 12 Drawing Sheets

(51) Int. Cl.
 *A61B 1/045* (2006.01)
 *A61B 1/05* (2006.01)
 *A61B 1/06* (2006.01)
 *A61B 1/07* (2006.01)
 *A61B 1/12* (2006.01)

(52) U.S. Cl.
 CPC ............... *A61B 1/05* (2013.01); *A61B 1/063* (2013.01); *A61B 1/0655* (2022.02); *A61B 1/0676* (2013.01); *A61B 1/0684* (2013.01); *A61B 1/07* (2013.01); *A61B 1/128* (2013.01)

(56) References Cited

U.S. PATENT DOCUMENTS

| | | | |
|---|---|---|---|
| 4,535,758 A | 8/1985 | Longacre, Jr. |
| 4,616,636 A | 10/1986 | Nagashima et al. |
| 4,643,022 A | 2/1987 | Werlberger et al. |
| 4,737,842 A | 4/1988 | Nagasaki |
| 4,782,386 A | 11/1988 | Ams et al. |
| 4,791,479 A | 12/1988 | Ogiu et al. |
| 4,807,291 A | 2/1989 | Hoffmann et al. |
| 4,878,112 A | 10/1989 | Ieoka |
| 4,953,539 A | 9/1990 | Nakamura et al. |
| 5,697,885 A | 12/1997 | Konomura et al. |
| 5,739,847 A | 4/1998 | Tranchita et al. |
| 6,061,591 A | 5/2000 | Freitag et al. |
| 6,110,106 A | 8/2000 | MacKinnon et al. |
| 6,377,346 B1 | 4/2002 | Vaisala et al. |
| 6,388,702 B1 | 5/2002 | Konomura et al. |
| 6,413,207 B1 | 7/2002 | Minami |
| 6,426,776 B1 | 7/2002 | Ochi |
| 6,698,907 B1 | 3/2004 | Alahautala et al. |
| 6,730,019 B2 | 5/2004 | Irion |
| 6,734,893 B1 | 5/2004 | Hess et al. |
| 7,041,054 B2 | 5/2006 | Klootz |
| 7,133,079 B2 | 11/2006 | Gleim |
| 7,339,151 B2 | 3/2008 | Mabuchi |
| D579,563 S | 10/2008 | Hensler et al. |
| 7,544,163 B2 | 6/2009 | MacKinnon et al. |
| 7,561,185 B2 | 7/2009 | Yamasaki et al. |
| 7,566,808 B2 | 7/2009 | Rando |
| 7,626,621 B2 | 12/2009 | Ito et al. |
| 7,654,952 B2 | 2/2010 | Ott |
| 7,663,677 B2 | 2/2010 | Shiraishi |
| 7,692,784 B2 | 4/2010 | MacKinnon |
| 7,727,555 B2 | 6/2010 | DiCarlo et al. |
| 7,796,319 B2 | 9/2010 | MacKinnon et al. |
| 8,018,589 B2 | 9/2011 | MacKinnon et al. |
| 8,031,233 B2 | 10/2011 | Mabuchi |
| 8,068,898 B2 | 11/2011 | Mycek et al. |
| 8,092,376 B2 | 1/2012 | Suda |
| 8,100,826 B2 | 1/2012 | MacKinnon et al. |
| 8,197,401 B2 | 6/2012 | Irion et al. |
| 8,417,324 B2 | 4/2013 | Mycek et al. |
| 8,570,635 B2 | 10/2013 | MacKinnon et al. |
| 8,764,224 B2 | 7/2014 | Tong |
| 9,257,468 B2 | 2/2016 | Gomi et al. |
| 9,516,239 B2 | 12/2016 | Blanquart et al. |
| 9,641,815 B2 | 5/2017 | Richardson et al. |
| 9,733,550 B2 | 8/2017 | Yamamoto et al. |
| 9,762,879 B2 | 9/2017 | Blanquart et al. |
| 9,777,913 B2 | 10/2017 | Talbert et al. |
| 9,888,199 B2 | 2/2018 | Gomi et al. |
| 10,084,944 B2 | 9/2018 | Henley et al. |
| 10,194,110 B2 | 1/2019 | Gomi et al. |
| 10,205,877 B2 | 2/2019 | Richardson et al. |
| 10,206,561 B2 | 2/2019 | Wichem et al. |
| 10,251,530 B2 | 4/2019 | Henley et al. |
| 10,277,875 B2 | 4/2019 | Blanquart et al. |
| 10,441,152 B2 | 10/2019 | Pauker |
| 10,499,803 B2 | 12/2019 | Bos et al. |
| 10,568,496 B2 | 2/2020 | Blanquart et al. |
| 10,667,669 B2 | 6/2020 | Watanabe |
| 10,670,248 B2 | 6/2020 | Talbert et al. |
| 10,785,461 B2 | 9/2020 | Blanquart et al. |
| 10,792,430 B2 | 10/2020 | Richter et al. |
| 10,888,218 B2 | 1/2021 | Wang |
| 10,911,649 B2 | 2/2021 | Henley et al. |
| 10,917,562 B2 | 2/2021 | Richardson et al. |
| 11,022,859 B2 | 6/2021 | Torobu |
| 11,070,779 B2 | 7/2021 | Blanquart et al. |
| 11,083,367 B2 | 8/2021 | Blanquart et al. |
| 11,095,816 B2 | 8/2021 | Senda |
| 11,185,213 B2 | 11/2021 | Henley et al. |
| 2006/0171693 A1* | 8/2006 | Todd ................... G03B 29/00 396/17 |
| 2009/0281390 A1 | 11/2009 | Qiu et al. |
| 2010/0324374 A1 | 12/2010 | Kim et al. |
| 2014/0364692 A1 | 12/2014 | Salman et al. |
| 2016/0367124 A1* | 12/2016 | Nishio ................ A61B 1/0638 |
| 2018/0039063 A1* | 2/2018 | Yamae ............... G02B 27/0916 |
| 2019/0142265 A1* | 5/2019 | Bos ................... A61B 1/00006 600/188 |
| 2020/0345222 A1* | 11/2020 | Ishizeki ............. A61B 1/00006 |

FOREIGN PATENT DOCUMENTS

| | | |
|---|---|---|
| JP | 2004097442 A | 4/2004 |
| KR | 100602498 B1 | 7/2006 |
| KR | 101739050 B1 | 5/2017 |

OTHER PUBLICATIONS

Mehta et al., "Current Role of Stroboscopy in Laryngeal Imaging", Current Opinion in Otolaryngology & Head and Neck Surgery, vol. 20, No. 6, Dec. 2012, pp. 429-436.

PCT/US2022/022884, "Invitation to Pay Additional Fees And, Where Applicable Protest Fee", Aug. 1, 2022, 4 pages.

PCT/US2022/022884, "International Preliminary Report on Patentability", Oct. 19, 2023, 7 pages.

PCT/US2022/022884, "International Search Report and the Written Opinion", Sep. 22, 2022, 16 pages.

* cited by examiner

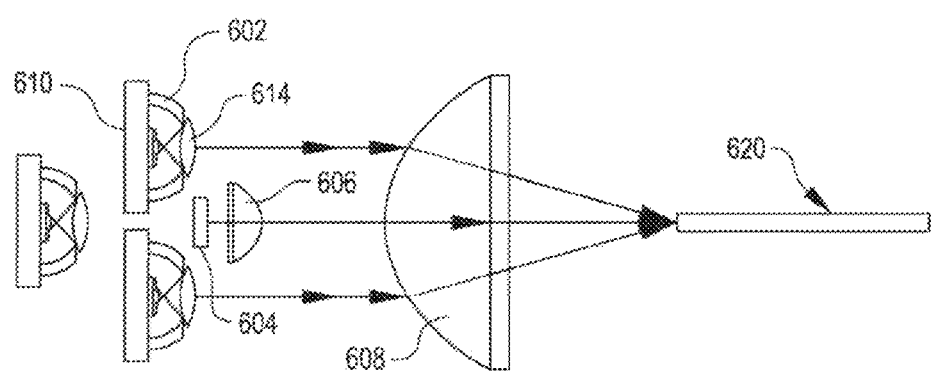

Patient Fundamental Phonation frequency 60 Hz - Pulse 300 us (1x300=300 us/frame)

Patient Fundamental Phonation frequency 120 Hz - 2 Pulse 150 us (2x150us = 300 us/frame)

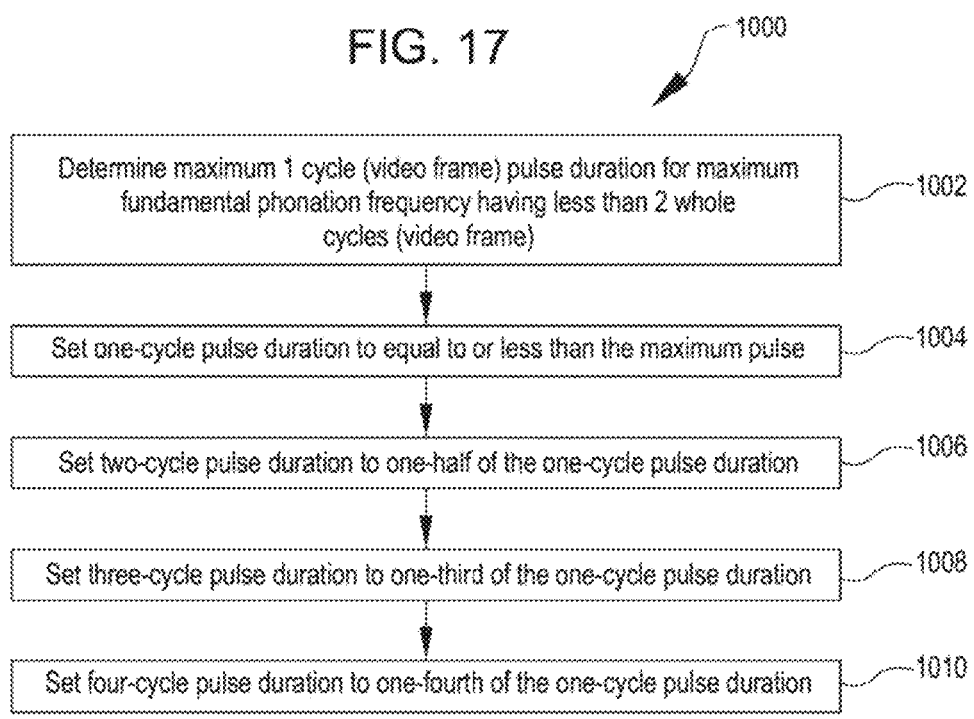

LARYNGEAL STROBOSCOPE UTILIZING SOLID STATE LIGHT SOURCES

RELATED APPLICATIONS

This application claims priority to U.S. Provisional Application No. 63/171,666, filed Apr. 7, 2021. The contents of these earlier filed application is hereby incorporated by reference herein in its entirety.

BACKGROUND

A laryngeal stroboscope is used to generate sequence of images of a phonating larynx in such a way as to provide apparent slow motion video of the larynx for review by a treating professional. Many laryngeal stroboscopes generate stroboscopic illumination of a phonating larynx during imaging of the larynx by an electronic camera and ridged or flexible Laryngeal Scope. The pulse timing of the stroboscopic light can be controlled to synchronize each pulse with a derived fundamental frequency of the sound produced by the phonating larynx (e.g., obtained by a laryngeal microphone).

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein are directed to stroboscopic endoscope systems and related methods. In many embodiments, one or more approaches are used to increase the amount of stroboscopic light generated by one or more LEDs and/or to increase the amount of stroboscopic light generated by one or more LEDs that is emitted by an endoscope to provide illumination of an object (e.g., a phonating larynx) for imaging of the object.

For example, in many embodiments, a stroboscopic endoscope system is configured to generate multiple light flashes during a video frame to repeatedly illuminate matching segments of vocal cord displacement cycles that occur during the video frame so as to increase the total amount of light used to illuminate the vocal cord during the video frame. Additionally, image blurring can be inhibited or avoided by keeping the duration of the light flashes short enough to avoid image blurring and illuminating the same segment of the respective vocal cord segments with each of the light flashes.

In many embodiments, a stroboscopic endoscope system includes an endoscope, an imaging device, and one or more LEDs that are intermittently energized to generate a sequence of light flashes emitted by the endoscope to illuminate an object (e.g., a phonating larynx) for imaging by imaging device. In many embodiments, the one or more LEDs are thermally coupled with a heat sink that is precooled prior to being intermittently energized. By precooling the heat sink, the one or more LEDs can be energized at a higher power level (which produces greater amount of light) without detrimental impact on the resulting operational life of the one or more LEDs due to the resulting increased cooling of the one or more LEDs.

In many embodiments, a stroboscopic endoscope system includes an endoscope, an imaging device, one or more LEDs, and a light redirecting assembly. The one or more LEDs are intermittently energized to generate a sequence of light flashes emitted by the endoscope to illuminate an object (e.g., a phonating larynx) for imaging by imaging device. In many embodiments, the light redirecting assembly is configured to increase the amount of light that is generated by the one or more LEDs that is emitted by the endoscope to provide illumination of an object (e.g., a phonating larynx) for imaging of the object. For example, in some embodiments, the light redirecting assembly comprises one or more hemispherical reflectors configured to increase the amount of light that is generated by the one or more LEDs that is emitted by the endoscope. In some embodiments, the light redirecting assembly comprises one or more total internal reflectors configured to increase the amount of light that is generated by the one or more LEDs that is emitted by the endoscope. By increasing the amount of the light generated by the one or more LEDs that is emitted by the endoscope, the one or more LEDs can have a reduced light output, thereby reducing cost and power consumption.

Thus, in one aspect, a stroboscopic endoscope system includes an endoscope, a video device, a first light emitting diode (LED), a light transmission assembly, a microphone, and a controller. The endoscope includes a light guide. The video device is configured for imaging vocal chords of a patient that are illuminated via the endoscope. The light transmission assembly is configured to transmit light generated by the first light source to the light guide. The microphone is configured to generate a microphone output signal in response to vocalization of the patient. The controller is operative coupled with the first light source, the video device, and the microphone. The controller is configured to process the microphone output signal to track a fundamental phonation frequency of the patient. The controller is configured to energize the first light source to generate a sequence of two or more light flashes in synchronization with the fundamental phonation frequency during a first video frame of the video device during which the vocal chords complete at least two complete displacement cycles so that the sequence of two or more light flashes illuminate matching segments of the at least two complete displacement cycles. The controller can be further configured to energize the first light source to generate a single light flash in synchronization with the fundamental phonation frequency during a second video frame of the video device during which the vocal chords complete less than two complete displacement cycles so that the single light flash illuminates a selected segment of one displacement cycle of the less than two complete displacement cycles. In many embodiments, the single light flash has a single light flash duration. The sequence of two or more light flashes can consist of two light flashes. Each of the two light flashes can have any suitable duration, for example, a duration equal to one-half of the single light flash duration.

The controller can be further configured to energize the first light source to generate a sequence of three or more light flashes in synchronization with the fundamental phonation frequency during a third video frame of the video device during which the vocal chords complete at least three complete displacement cycles so that the sequence of three or more light flashes illuminate matching segments of the at least three complete displacement cycles. The sequence of three or more light flashes can consist of three light flashes.

Each of the three light flashes can have any suitable duration, for example, a duration equal to one-third of the single light flash duration.

The controller can be further configured to energize the first light source to generate a sequence of four or more light flashes in synchronization with the fundamental phonation frequency during a fourth video frame of the video device during which the vocal chords complete at least four complete displacement cycles so that the sequence of four or more light flashes illuminate matching segments of the at least four complete displacement cycles. The sequence of four or more light flashes can consist of four light flashes. Each of the four light flashes can have any suitable duration, for example, a duration equal to one-fourth of the single light flash duration.

The stroboscopic endoscope system can further include a heat sink and a thermoelectric cooler. The heat sink can be coupled with the first light source to transfer heat generated by the first light source to the heat sink. The thermoelectric cooler can be coupled with the heat sink and operable to remove heat from the heat sink. The controller can be operative coupled with the thermoelectric cooler and configured to operate the thermoelectric cooler to cool the heat sink to below an ambient temperature of air surrounding the heat sink prior to energizing the first light source to generate the sequence of light flashes. The heat sink can be cooled to any suitable temperature below ambient temperature, for example, at least 5 degrees Celsius below the ambient temperature, or at least 10 degrees Celsius below the ambient temperature.

The stroboscopic endoscope system can further include a hemispherical reflector configured to redirect light generated by the first light source into the light transmission assembly for transmission to the light guide. The stroboscopic endoscope system can further include an image processor configured to perform color balancing of images captured via the endoscope to compensate for a first shift in spectrum induced by the hemispherical reflector. The first light source can include a phosphor coating configured to emit white light.

The stroboscopic endoscope system can further include a total internal reflector configured to redirect light generated by the first light source into the light transmission assembly via total internal reflection for transmission to the endoscope for emission by the endoscope. The first light source can be configured to generate monochromatic light. The light transmission assembly can include ceramic phosphors. In some embodiments, the sequence of light flashes excite the ceramic phosphors so as to generate a sequence of white light flashes that are transmitted to the light guide. In some embodiments, the ceramic phosphors are excited in a reflective mode. In some embodiments, the ceramic phosphors are excited in a transmissive mode.

In another aspect, a stroboscopic endoscope system includes an endoscope, a video device, a first light source, a second light source, a light transmission assembly, and a controller. The endoscope includes a light guide. The video device is configured for imaging vocal chords of a patient that are illuminated via the endoscope. The light transmission assembly is configured to transmit light generated by the first light source and the second light source to the light guide. The light transmission assembly includes a converging lens configured to converge each of light generated by the first light source and light generated by the second light source into the light guide. The controller is operative coupled with the first light source and configured to energize the first light source to generate a sequence of light flashes used to illuminate the vocal chords of the patient.

The stroboscopic endoscope system can include a heat sink and a thermoelectric cooler. The heat sink can be coupled with the first light source and the second light source to transfer heat generated by the first light source and the second light source to the heat sink. The thermoelectric cooler can be coupled with the heat sink and operable to remove heat from the heat sink. The controller can be operative coupled with the thermoelectric cooler and configured to operate the thermoelectric cooler to cool the heat sink to below an ambient temperature of air surrounding the heat sink prior to energizing the first light source and the second light source to generate the sequence of light flashes. The heat sink can be cooled to any suitable temperature below the ambient temperature. For example, the heat sink can cooled to at least 5 degrees Celsius below the ambient temperature, or to at least 10 degrees Celsius below the ambient temperature.

The stroboscopic endoscope system can include a first hemispherical reflector and a second hemispherical reflector. The first hemispherical reflector can be configured to redirect light generated by the first light source into the light transmission assembly for transmission to the endoscope. The second hemispherical reflector can be configured to redirect light generated by the second light source into the light transmission assembly for transmission to the endoscope. The stroboscopic endoscope system can further include an image processor configured to perform color balancing of images captured via the endoscope to compensate for a shift in spectrum induced by the first hemispherical reflector and the second hemispherical reflector. In some embodiments, each of the first light source and the second light source include a phosphor coating configured to emit white light.

The stroboscopic endoscope system can include a first total internal reflector and a second total internal reflector. The first total internal reflector can be configured to redirect light generated by the first light source into the light transmission assembly via total internal reflection for transmission into the light guide. The second total internal reflector configured to redirect light generated by the second light source into the light transmission assembly via total internal reflection for transmission into the light guide.

Each of the first light source and the second light source can be configured to generate monochromatic light. The light transmission assembly can include ceramic phosphors. In some embodiments, the sequence of light flashes excite the ceramic phosphors so as to generate a sequence of white light flashes that are transmitted to the endoscope. In some embodiments, the ceramic phosphors are excited in a reflective mode. In some embodiments, the ceramic phosphors are excited in a transmissive mode.

In another aspect, a stroboscopic endoscope system includes an endoscope, an imaging device, a first light source, a light transmission assembly, a heat sink, a thermoelectric cooler, and a controller. The endoscope includes a light guide The imaging device is configured for imaging an object illuminated via the endoscope. The light transmission assembly is configured to transmit light generated by the first light source into the light guide. The heat sink is coupled with the first light source to transfer heat generated by the first light source to the heat sink. The thermoelectric cooler is coupled with the heat sink and operable to remove heat from the heat sink. The controller is operative coupled with the first light source and the thermoelectric cooler. The controller is configured to energize the first light source to generate a sequence of light flashes. The controller is configured to operate the thermoelectric cooler to cool the heat sink to below an ambient temperature of air surrounding the heat sink prior to energizing the first light source to generate the sequence of light flashes.

The heat sink can be cooled to any suitable temperature below the ambient temperature. For example, in some embodiments, the heat sink is cooled to at least 5 degrees Celsius below the ambient temperature. In some embodiments, the heat sink is cooled to at least 10 degrees Celsius below the ambient temperature.

As a result of the precooling of heat sink prior to energizing the first light source to generate the sequence light, the first light source can be energized at a higher power while maintaining a suitable operational life expectancy due to increased cooling of the first light source. For example, in some embodiments, the first light source has a maximum recommended power level for continuous energization, a stroboscopic power level is intermittently applied to the first light source to generate the sequence of light flashes, and the stroboscopic power level is at least four times the maximum recommended power level. In some embodiments, the stroboscopic power level is at least eight times the maximum recommended power level.

The stroboscopic endoscope system can include any suitable number of LEDs that are intermittently energized to generate the sequence of light flashes. For example, in many embodiments, the stroboscopic endoscope system includes a second light source. The heat sink can be coupled with the second light source to transfer heat generated by the second light source to the heat sink. The controller can be configured to energize the second light source in conjunction with the first light source to generate the sequence of light flashes.

The stroboscopic endoscope system can be configured to increase the amount of light that is generated by the first light source (and by the second light source when included) that is emitted by the endoscope. For example, the stroboscopic endoscope system can further include a hemispherical reflector configured to redirect light generated by the first light source into the light transmission assembly for transmission into the light guide. In some embodiments, the stroboscopic endoscope system can include an image processor configured to perform color balancing of images captured via the endoscope to compensate for a first shift in spectrum induced by the first hemispherical reflector. In some embodiments, the first light source comprises a phosphor coating configured to emit white light. The stroboscopic endoscope system can further include a total internal reflector configured to redirect light generated by the first light source into the light transmission assembly via total internal reflection for transmission into the light guide.

The first light source (and the second light source when included) can have any suitable configuration. For example, in many embodiments, the first light source is configured to generate monochromatic light, the light transmission assembly can include ceramic phosphors, and the sequence of light flashes excite the ceramic phosphors so as to generate a sequence of white light flashes that are transmitted into the light guide. In some embodiments, the ceramic phosphors are excited in a reflective mode. In some embodiments, the ceramic phosphors are excited in a transmissive mode.

In another aspect, a method of capturing stroboscopic images includes operating a thermoelectric cooler to cool a heat sink to below an ambient temperature of air surrounding the heat sink. Subsequent to the heat sink being cooled to below the ambient temperature, a first light source is energized to generate a sequence of light flashes. The first light source is thermally coupled to the heat sink to cool the first light source during the generation of the sequence of light flashes. Light from the sequence of light flashes is transmitted into a light guide of an endoscope. Light from the sequence of light flashes is emitted by the endoscope. Images of an object illuminated by the light emitted by the endoscope are captured.

In many embodiments of the method, the heat sink is cooled to at least 5 degrees Celsius below the ambient temperature. In some embodiments of the method, the heat sink is cooled to at least 10 degrees Celsius below the ambient temperature.

In many embodiments of the method, the first light source is energized using a power level substantially higher than a continuous operation power level. For example, in many embodiments, the first light source has a maximum recommended power level for continuous operation, a stroboscopic power level is intermittently applied to the first light source to generate the sequence of light flashes, and the stroboscopic power level is at least four times the maximum recommended power level. In some embodiments of the method, the stroboscopic power level is at least eight times the maximum recommended power level.

In many embodiments of the method, two or more LEDs are energized to generate the sequence of light flashes. For example, in many embodiments of the method, subsequent to the heat sink being cooled to below the ambient temperature, a second light source is energized in conjunction with the first light source to generate the sequence of light flashes. The second light source can be thermally coupled to the heat sink to cool the second light source during the generation of the sequence of light flashes.

In many embodiments of the method, some of the light generated by the first light source that would not otherwise be directed so as to be transmitted through and emitted by the endoscope is redirected so as to be transmitted through and emitted by the endoscope, thereby increasing the percentage of the light generated by the first light source that is emitted by the endoscope instead of being wasted. For example, in some embodiments, the method includes redirecting light generated by the first light source by a hemispherical reflector for transmission into the light guide. In some embodiments, the method includes performing color balancing of images captured via the endoscope by an image processor to compensate for a first shift in spectrum induced by the hemispherical reflector. In some embodiments of the method, the first light source includes a phosphor coating configured to emit white light. In some embodiments, the method includes redirecting light generated by the first light source via total internal reflection for transmission into the light guide.

The first light source (and the second light source when included) can have any suitable configuration. For example, in many embodiments of the method, the first light source is configured to generate monochromatic light, the light transmission assembly can include ceramic phosphors, and the sequence of light flashes excite the ceramic phosphors so as to generate a sequence of white light flashes that are transmitted into the light guide. In some embodiments of the method, the ceramic phosphors are excited in a reflective mode. In some embodiments of the method, the ceramic phosphors are excited in a transmissive mode.

In another aspect, a stroboscopic endoscope system includes an endoscope, an imaging device, a first light source, a light transmission assembly, a hemispherical reflector, and a controller. The endoscope includes a light guide. The imaging device is configured for imaging an object illuminated via the endoscope. The light transmission assembly is configured to transmit light generated by the first light source into the light guide. The hemispherical reflector is configured to redirect light generated by the first light source into the light transmission assembly for transmission into the light guide. The controller is operative coupled with the first light source. The controller is configured to energize the first light source to generate a sequence of light flashes.

In another aspect, a stroboscopic endoscope system includes an endoscope, an imaging device, a first light source, a light transmission assembly, a total internal reflector, and a controller. The endoscope includes a light guide. The imaging device is configured for imaging an object illuminated via the endoscope. The light transmission assembly is configured to transmit light generated by the first light source into the light guide. The total internal reflector is configured to redirect light generated by the first light source via total internal reflection for transmission into the light guide. The controller is operative coupled with the first light source. The controller is configured to operate the first light source to generate a sequence of light flashes.

For a fuller understanding of the nature and advantages of the present invention, reference should be made to the ensuing detailed description and accompanying drawings.

BRIEF DESCRIPTION OF THE DRAWINGS

FIGS. 8 and 9 illustrate another embodiment of a stroboscopic light assembly that can be employed in the stroboscopic endoscope system of FIG. 1.

FIG. 17 is a simplified schematic diagram of a method of setting light pulse durations that can be employed in the approach of FIGS. 14A through 16D.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments described herein are directed to a stroboscope (e.g., a laryngeal stroboscope) with LED generated stroboscopic light source. In some embodiments, the stroboscope is a laryngeal stroboscope is configured to provide stroboscopic illumination of a phonating larynx during imaging of the larynx by an electronic camera and ridged or flexible Laryngeal Scope. In preferred embodiments, the pulse timing of the stroboscopic light is controlled to synchronize each pulse with a video frame of the electronic camera and a derived fundamental frequency of the sound produced by the phonating larynx (e.g., obtained by a laryngeal microphone) in such a way as to provide apparent slow motion video of the larynx for review by a treating professional. In preferred embodiments, the system that presents the final strobe image has the capability to provide automatic color balancing in order to provide a high quality image for clinical use.

Figure 1:
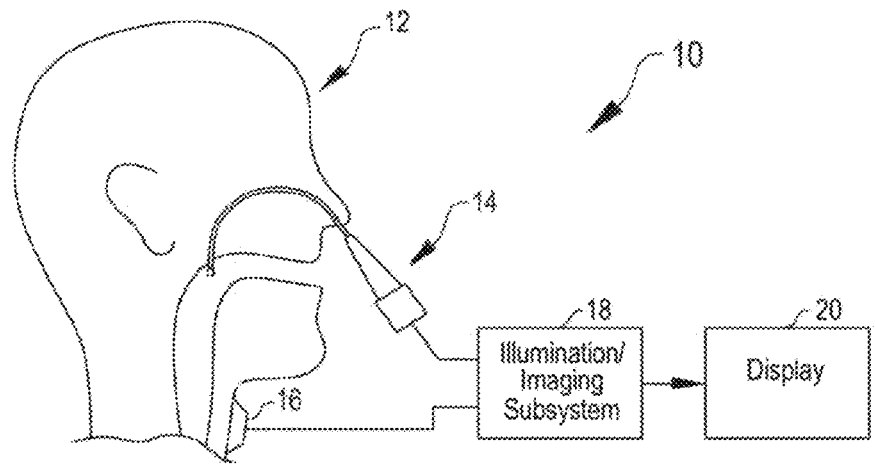
FIG. 1 diagrammatically illustrates a stroboscopic endoscope system, in accordance with embodiments.

Turning now to the drawing figures, in which like reference numbers refer to like elements in the various figures, FIG. 1 diagrammatically illustrates a stroboscopic endoscope system 10, in accordance with embodiments, being used for imaging of a phonating larynx of a patient 12. The stroboscopic endoscope system 10 includes an endoscope 14, a laryngeal microphone 16, an illumination/imaging subsystem 18, and a display 20. In the illustrated configuration, the laryngeal microphone 16 is interfaced with the throat of the patient 12 near the larynx for detecting the patient's vocalization (e.g., speech, singing, certain tones as requested by the medical professional conducting the examination) during imaging of the phonating larynx. The laryngeal microphone 16 can, however, be mounted at any suitable location for detecting the patient's vocalization. In the illustrated configuration, the endoscope 14 is shown positioned for illuminating the larynx with stroboscopic light emitted from the endoscope 14 and generating image data of the larynx. The endoscope 14 is connected to the illumination/imaging subsystem 18 by a suitable cable 22 via which the illumination/imaging subsystem 18 transmits a stroboscopic sequence of light flashes to the endoscope 14 for emission by the endoscope 14 to illuminate the larynx and receives image data from an endoscope imaging device included in the endoscope 14. The laryngeal microphone 16 is connected to the illumination/imaging subsystem 18 via a suitable microphone cable 24 for receiving audio data or output signal generated by the laryngeal microphone 16.

The illumination/imaging subsystem 18 includes a stroboscopic light assembly that includes one or more light emitting diodes (LEDs) that are controllably energized to generate the sequence of light flashes based on the output of the laryngeal microphone 16 so as to synchronize the light flashes with a base frequency of the phonating larynx. In many embodiments, the cable 22 includes a flexible light guide (e.g., a flexible optical cable including one or more optical fibers) and light generated by the one or more LEDs is coupled into the flexible light guide. The flexible light guide transmits the sequence of light flashes to the endoscope 14, which emits the stroboscopic light to intermittently illuminate the phonating larynx.

In many embodiments, the illumination/imaging subsystem 18 process the image data received from the endoscope 14 to generate apparent slow motion video of the larynx for review by a treating professional. In preferred embodiments, the illumination/imaging subsystem 18 performs automatic color balancing in order to provide a high quality image for clinical use. In the illustrated embodiments, the illumination/imaging subsystem 18 is operable to display the apparent slow motion video of the larynx on the display 20.

Figure 2:
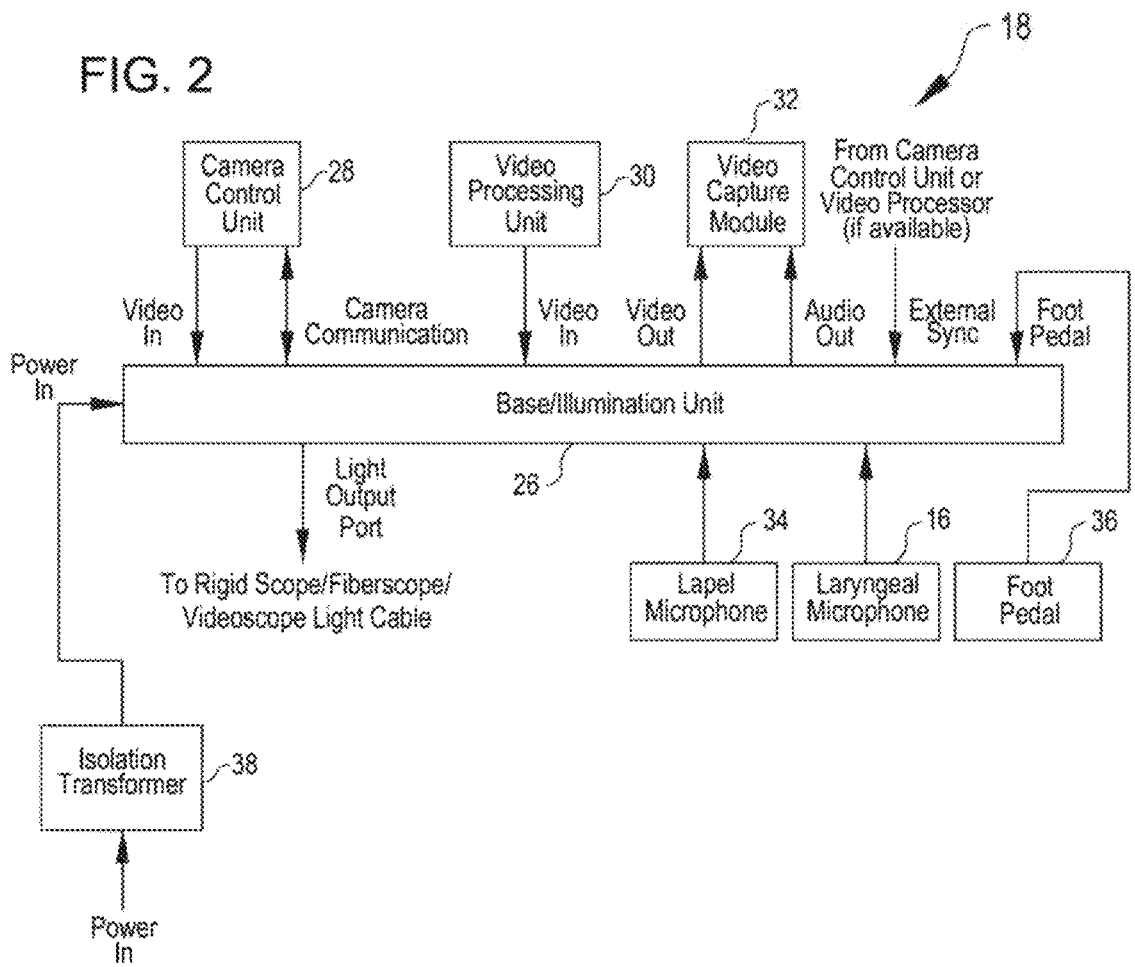
FIG. 2 diagrammatically illustrates an embodiment of the illumination/imaging subsystem of FIG. 1.

FIG. 2 diagrammatically illustrates an embodiment of the illumination/imaging subsystem 18 of FIG. 1. In the illustrated embodiment, the illumination/imaging subsystem 18 includes a base/illumination unit 26, a camera control unit 28, a video processing unit 30, a video capture module 32, a lapel microphone 34, the laryngeal microphone 16, a foot pedal 36, and an isolation power transformer 38. The base/illumination unit 26 processes output generated by the laryngeal microphone 16 to determine and track the base frequency of the vocalization of the patient 12. The base/illumination unit 26 includes one or more LEDs to generate a stroboscopic sequence of light flashes by intermittently energizing the one or more LEDs based on the tracked based frequency to sequentially illuminate the larynx at a progressing sequence of stages of the larynx during the vibration of the larynx. The camera control unit 28 controls operation of the endoscope imaging device of the endoscope 14 and provides video of the phonating larynx to the base/illumination unit 26. The video processing unit 30 processes image data generated by the endoscope imaging device and provides the processed video to the base/illumination unit 26. Video input supplied to the base/illumination unit 26 by the camera control unit 28 and/or by the video processing unit 30 is output to the video capture module 32. The base/illumination unit 26 also outputs an audio output to the video capture module 32. The audio output provided to the video capture module 32 can include an audio output generated by the lapel microphone 34 and/or an audio output generated by the laryngeal microphone 16 for the purpose of context to video of the phonating larynx captured by the endoscopic system 10. The video capture module 32 is configured to generate and store the apparent slow motion video of the larynx for review by a treating professional.

The base/illumination unit 26 can include one or more LEDs that are overdriven (relative to the corresponding manufacturer's maximum power level for the LED(s)) to produce short (e.g., nominal 120 us) intense white light pulses (e.g., with a repetition rate of 60 pulses per second) used to "freeze" the motion of the phonating larynx. In some envisioned embodiments, the LED(s) are overdriven by 4 to 12 times the manufacturer's maximum power level for the LED(s). The overdriving of the LED(s) may be further characterized in terms of a ratio of instantaneous power applied to the LED(s) to light emitting area of the LED(s). In some envisioned embodiments, the ratio of instantaneous power applied to the LED(s) to light emitting area of the LED(s) is 4 to 12 times a ratio corresponding to the manufacturer's maximum power level for the LED(s). In some embodiments, the LED(s) are blue LASER Diodes(s) that generate 450 nm wavelength light used to excite ceramic phosphors to produce the white light. In some embodiments, the LED(s) are LASER Diodes(s). In many embodiments, the LED(s) generate non-collimated light.

The base/illumination unit 26 can include a cooling mechanism used to pre-cool the LED(s) and/or an associated heat sink thermally coupled with the LED(s) prior to an imaging session. For example, in some envisioned embodiments, the base/illumination unit 26 includes a Peltier heat pump (aka, thermoelectric cooler), which can be used to pre-cool the LED(s) below ambient temperatures and/or a heat sink thermally coupled with the LED(s).

Stroboscopic Light Assemblies

In many embodiments, the stroboscopic light assembly of the base/illumination unit 26 is configured to accommodate the application of higher power to the one or more LEDs via precooling of a heat sink coupled with the one or more LEDs. In many embodiments, the stroboscopic light assembly includes a light redirection assembly that redirects some of the light generated by the one or more LEDs that would not otherwise be directed so as to be transmitted through and emitted by the endoscope so as to be transmitted through and emitted by the endoscope, thereby increasing the percentage of the light generated by the one or more LEDs that is emitted by the endoscope instead of being wasted. In many embodiments, both the precooling of the heat sink and the light redirection assembly are employed.

The LED(s) can be blue LASER Diodes that excite ceramic phosphors so as to cause the ceramic phosphors to emit white light flashes for emission by the endoscope 14 to illuminate a phonating larynx. For example, in some embodiments the LED(s) can be blue LASER Diodes that excite ceramic phosphors in a reflective mode as illustrated in FIG. 3.

Figure 3:
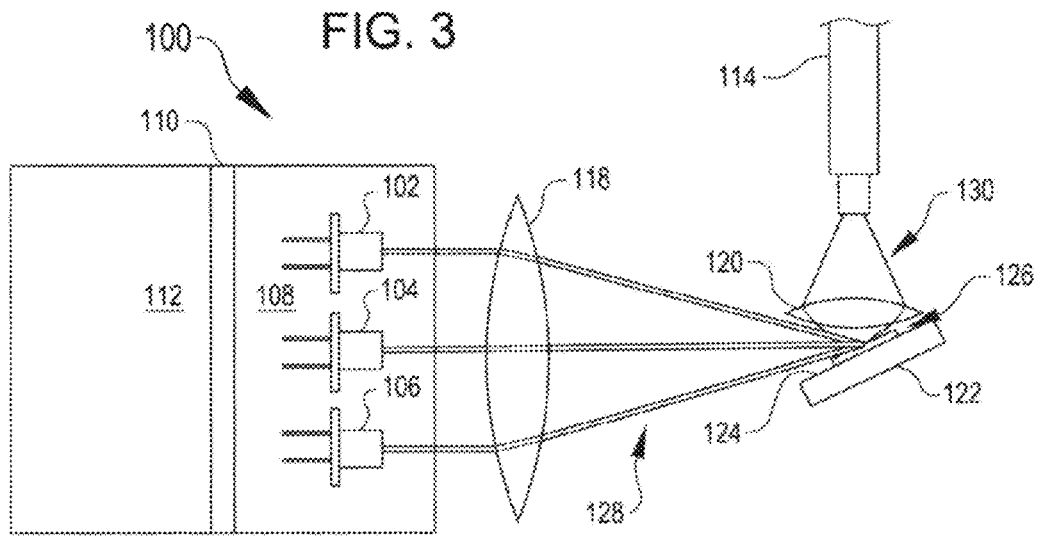
FIG. 3 diagrammatically illustrates an embodiment of a stroboscopic light assembly that can be employed in the illumination/imaging subsystem of FIG. 1.

FIG. 3 diagrammatically illustrates a stroboscopic light assembly 100 that can be included in the base/illumination unit 26. The light assembly 100 includes LEDs 102, 104, 106, a heat sink 108, a thermoelectric cooler 110, a heat exchanger 112, an endoscopic light guide 114, and a light coupling assembly 116. The LEDs 102, 104, and 116 are intermittently and concurrently energized to generate a sequence of light flashes that are coupled into the endoscopic light guide 114 by the light coupling assembly 116.

The light coupling assembly 116 includes lenses 118, 120 and reflective phosphor assembly 122. The reflective phosphor assembly 122 has a reflective surface 124 and a phosphor coating 126 on the reflective surface 124. In the illustrated embodiment, the LEDs 102, 104, 106 emit a sequence of 450 nm wavelength light flashes 128. The lens 118 focuses 450 nm wavelength light flashes 128 emitted by the LEDs 102, 104, 106 onto the phosphor coating 126. The phosphor coating 126 is excited by the 450 nm light flashes 128 and thereby emits a sequence of white light flashes 130. The reflective surface 124 reflects some of the white light flashes 130 emitted by the phosphor coating 126 towards the lens 120. Accordingly, the phosphor coating 126 is excited in a reflective mode. The lens 120 focuses much of the white light flashes 130 emitted by the phosphor coating 126 into the endoscopic light guide 114. The endoscopic light guide 114 transmits the white light flashes 130 to the endoscope 14, which emits the white light flashes 130 to illuminate the phonating larynx.

The LEDs 102, 104, 106 are thermally coupled with the heat sink 108 so that heat generated by the LEDs 102, 104, 106 during the intermittent energization of the LEDs 102, 104, 106 is transferred to the heat sink 108 via thermal conduction, thereby serving to increase cooling of the LEDs so that the LEDs can be energized at higher power levels as compared to lesser cooling of the LEDs. The thermoelectric cooler 110 is operable to transfer heat from the heat sink 108 to the heat exchanger 112. The heat exchanger 112 is configured to transfer heat to a suitable repository (e.g., ambient air, a suitable liquid coolant). In many embodiments, the thermoelectric cooler 110 is operated prior to energization of the LEDs 102, 104, 106 so as to cool the heat sink below the ambient temperature of air surrounding the heat sink 108 and/or the LEDs 102, 104, 106 prior to energizing the LEDs 102, 104, 106 to generate the sequence of light flashes. In some embodiments, the thermoelectric cooler 110 continues to be operated during the energization of the LEDs 102, 104, 106 to reduce the rate at which the temperature of the heat sink 108 increases during the energization of the LEDs 102, 104, 106. Junction temperatures reduction of up to 15 C for a single stage Peltier increasing heat transfer from the LED are maintainable.

Figure 4:
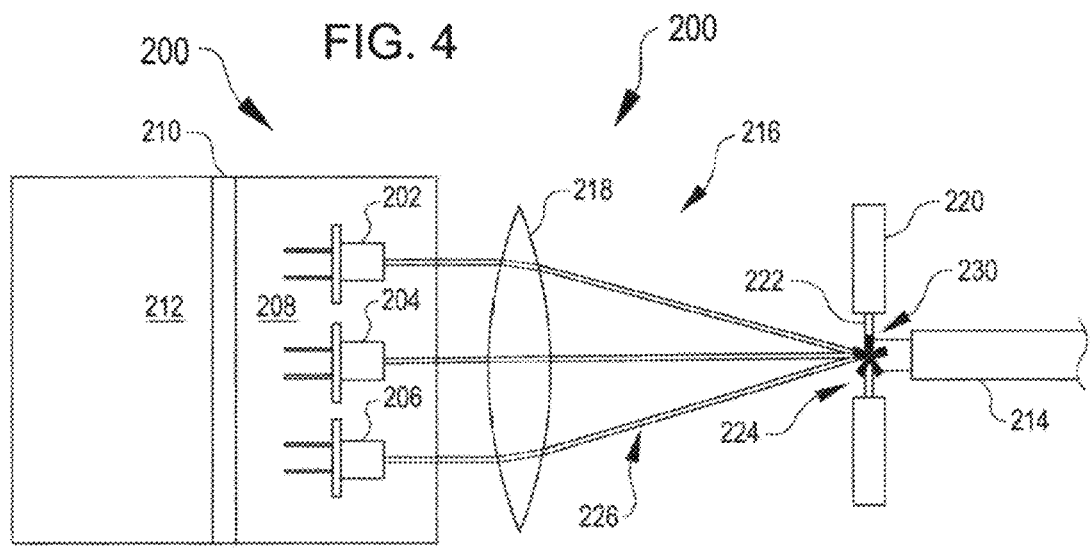
FIG. 4 diagrammatically illustrates another embodiment of a stroboscopic light assembly that can be employed in the stroboscopic endoscope system of FIG. 1.

FIG. 4 diagrammatically illustrates a stroboscopic light assembly 200 that can be included in the base/illumination unit 26. The light assembly 200 includes LEDs 202, 204, 206, a heat sink 208, a thermoelectric cooler 210, a heat exchanger 212, an endoscopic light guide 214, and a light coupling assembly 216. The LEDs 102, 104, and 116 are intermittently and concurrently energized to generate a sequence of light flashes that are coupled into the endoscopic light guide 214 by the light coupling assembly 216.

The light coupling assembly 216 includes a lens 218 and transmissive phosphor assembly 220. The transmissive phosphor assembly 220 has a transmissive element 222 and a phosphor coating 224 on the transmissive element 222. In the illustrated embodiment, the LEDs 202, 204, 206 emit a sequence of 450 nm wavelength light flashes 226. The lens 218 focuses 450 nm wavelength light flashes 226 emitted by the LEDs 202, 204, 206 onto the phosphor coating 224. The phosphor coating 224 is excited by the 450 nm light flashes 226 and thereby emits a sequence of white light flashes 230. The some of the white light flashes 230 emitted by the phosphor coating 224 are transmitted through the transmissive element 222 into the endoscopic light guide 214. Accordingly, the phosphor coating 224 is excited in a transmissive mode. The endoscopic light guide 214 transmits the white light flashes 230 to the endoscope 14, which emits the white light flashes 230 to illuminate the phonating larynx.

The LEDs 202, 204, 206 are thermally coupled with the heat sink 208 so that heat generated by the LEDs 202, 204, 206 during the intermittent energization of the LEDs 202, 204, 206 is transferred to the heat sink 208 via thermal conduction, thereby serving to increase cooling of the LEDs so that the LEDs can be energized at higher power levels as compared to lesser cooling of the LEDs. The thermoelectric cooler 210 is operable to transfer heat from the heat sink 208 to the heat exchanger 212. The heat exchanger 212 is configured to transfer heat to a suitable repository (e.g., ambient air, a suitable liquid coolant). In many embodiments, the thermoelectric cooler 210 is operated prior to energization of the LEDs 202, 204, 206 so as to cool the heat sink below the ambient temperature of air surrounding the heat sink 208 and/or the LEDs 202, 204, 206 prior to energizing the LEDs 202, 204, 206 to generate the sequence of light flashes. In some embodiments, the thermoelectric cooler 210 continues to be operated during the energization of the LEDs 202, 204, 206 to reduce the rate at which the temperature of the heat sink 208 increases during the energization of the LEDs 202, 204, 206.

Figure 5:
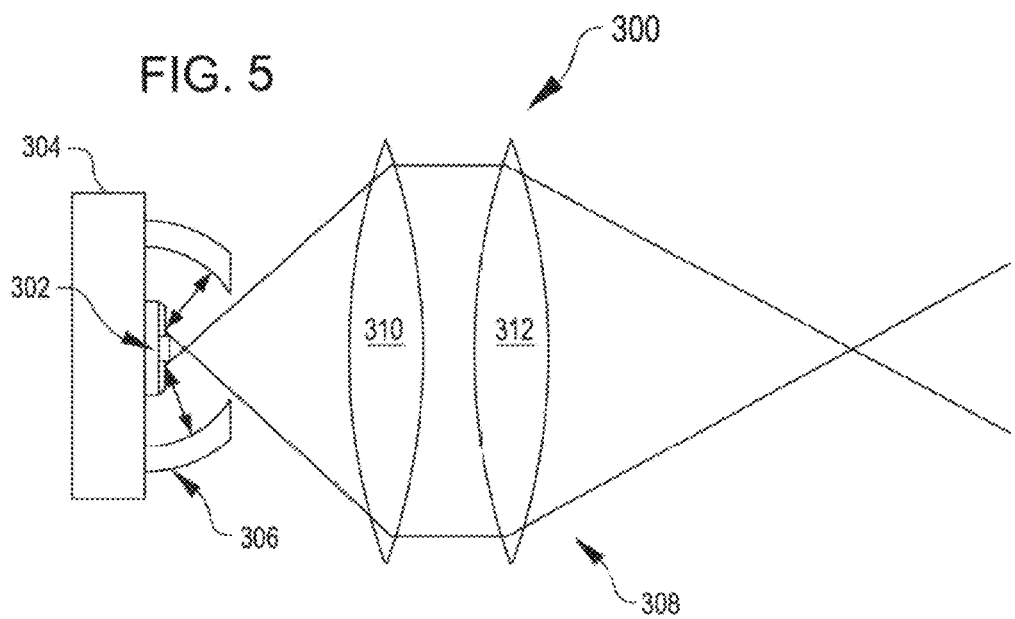
FIG. 5 diagrammatically illustrates another embodiment of a stroboscopic light assembly that can be employed in the stroboscopic endoscope system of FIG. 1.

FIG. 5 diagrammatically illustrates a stroboscopic light assembly 300 that can be included in the base/illumination unit 26. The light assembly 300 includes a phosphor coated blue LED 302, a reflective base 304, a hemispherical reflector 306, and a light coupling assembly 308. The phosphor coated blue LED 302 is mounted to the reflective base. The LED 302 is intermittently energized to generate a sequence of white light flashes that is coupled into the endoscope 14. In many embodiments, the reflective base 304 functions as a heat sink to absorb heat generated by the LED 302. In many embodiments, the light assembly 300 includes a thermoelectric cooler and heat exchanger as described herein in any of the light assemblies 100, 200 for precooling the reflective base 304.

The sequence of white light flashes emitted by the LED 302 is transmitted into the endoscope 14 via the reflective base 304, the hemispherical reflector 306, and the light coupling assembly 308. The reflective base 304 and the hemispherical reflector 306 are configured to redirect portions of the sequence of white light flashes emitted by the LED 302 that would not otherwise be incident onto the lens 310 so as to be incident on the lens 310, thereby increasing the amount of light from the sequence of white light flashes emitted by the LED 302 that is coupled into the endoscope 14. The video processing unit 30 can have the capability to automatically color balance for a shift in spectrum induced by the hemispherical reflector 306.

Figure 6:
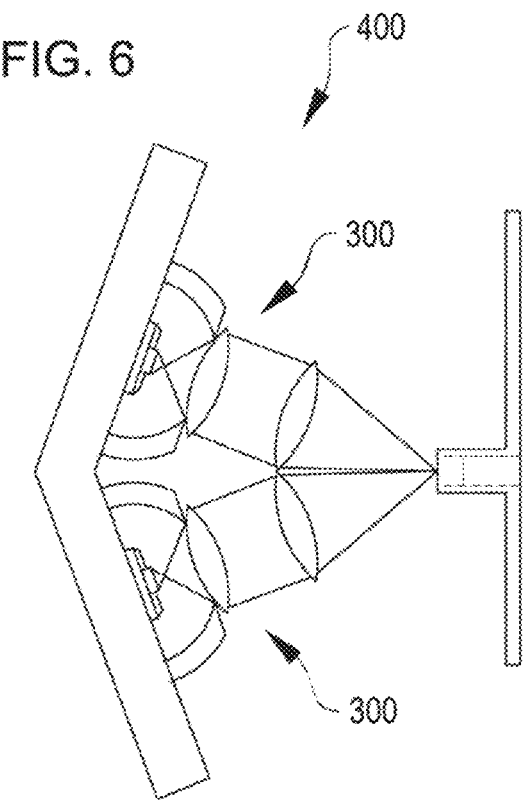
FIG. 6 diagrammatically illustrates another embodiment of a stroboscopic light assembly that can be employed in the stroboscopic endoscope system of FIG. 1.

FIG. 6 diagrammatically illustrates a stroboscopic light assembly 400 that can be included in the base/illumination unit 26. The light assembly 400 aggregates two of the light assemblies 300.

Figure 7A:
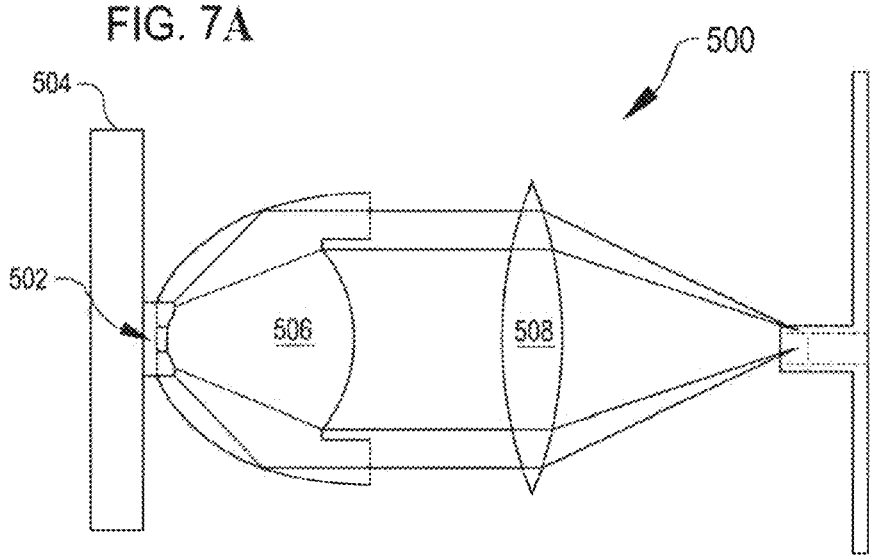
FIGS. 7A and 7B diagrammatically illustrate other embodiments of a stroboscopic light assembly that can be employed in the stroboscopic endoscope system of FIG. 1.

FIG. 7A diagrammatically illustrates a stroboscopic light assembly 500 that can be included in the base/illumination unit 26. The light assembly 500 includes a phosphor coated blue LED 502, a reflective base 504, a Total Internal Reflection (TIR) optical element 506, and a lens 508. The phosphor coated blue LED 502 is mounted to the reflective base 504. The LED 502 is intermittently energized to generate a sequence of white light flashes that is coupled into the endoscope 14. In many embodiments, the reflective base 504 functions as a heat sink to absorb heat generated by the LED 502. In many embodiments, the light assembly 500 includes a thermoelectric cooler and heat exchanger as described herein in any of the light assemblies 100, 200 for precooling the reflective base 504.

The sequence of white light flashes emitted by the LED 302 is transmitted into the endoscope 14 via the reflective base 504, the TIR optical element 506, and the lens 508. The reflective base 504 and the TIR optical element 506 are configured to redirect portions of the sequence of white light flashes emitted by the LED 502 that would not otherwise be incident onto the lens 508 so as to be incident on the lens 508, thereby increasing the amount of light from the sequence of white light flashes emitted by the LED 502 that is coupled into the endoscope 14. The TIR optical element 506 is externally shaped to redirect light emitted by the LED 502 onto the lens 508 via total internal reflection of the light within the TIR optical element 506.

Figure 7B:
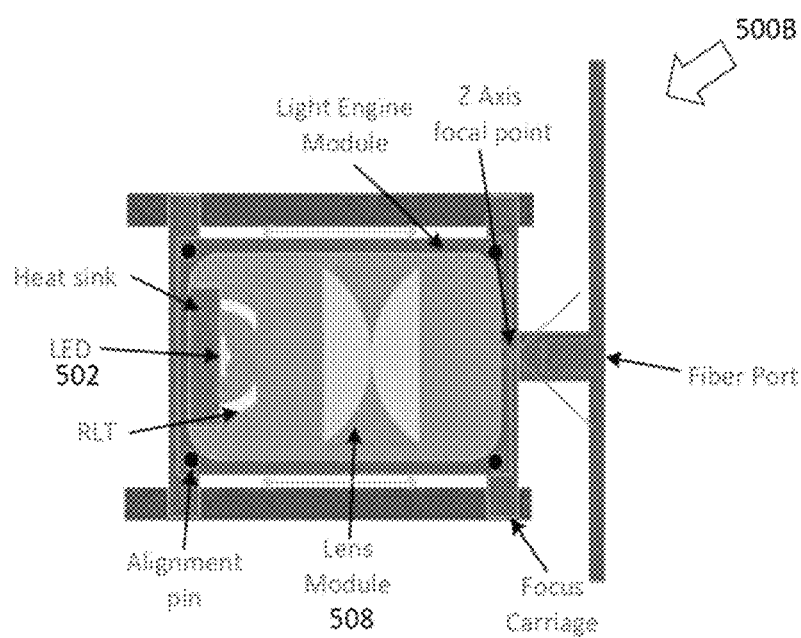

FIG. 7B depicts an alternate stroboscopic light assembly 500B embodiment that can be included in the base/illumination unit 26. The light assembly 500B includes a reflective light transmitter (RLT) 532, an LED light source 502, a heat sink 534, alignment pins 536, focus carriage 538, and a central lens module 508 with a collimating lens and a converging lens. This embodiment enables alignment of a light source such as LED 502 to the scope light guide, and may include fiber port 540. X and Y dimensions with respect to the optical axis (Z) are handled with a mechanical light engine module 520. The Z axis alignment may vary for scopes from different manufacturers. In some embodiments, Z axis alignment may be manual, with electro-mechanical adjustment under front panel controls, or a mechanical adjustment wheel. When electro-mechanical adjustment occurs, it may be an automatic adjustment using a Proportional Integral Derivative (PID) on the video input to optimize for maximum brightness. The automatic adjustment may further also be either as a setup function or a period adjustment used to optimize the field of illumination.

Figure 9:
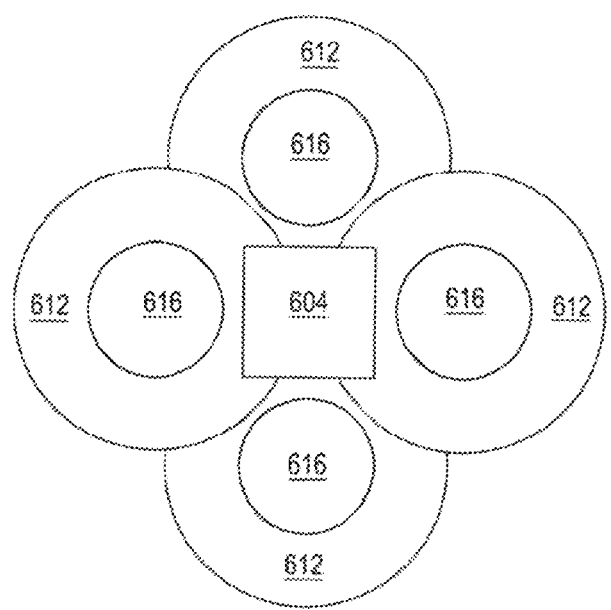

FIGS. 8 and 9 illustrate a stroboscopic light assembly 600 that can be included in the base/illumination unit 26. The light assembly 600 includes four reflective light transmitters (RLTs) 602, a central LED 604, a central collimating lens 606, and a shared converging lens 608. Each of the four RLTs 602 includes a reflective base 610, a hemispherical reflector 612, an LED 614, and a collimating lens 616. The hemispherical reflector 612 has a central aperture 618 through which light emitted by the LED 614 is transmitted to the collimating lens 616. Light emitted by the LED 614 onto the hemispherical reflector 612 or the reflective base 610 redirected by the hemispherical reflector 612 and/or the reflective base 610 so as to increase the amount of light emitted by the LED 614 that propagates through the collimating lens 616. The collimating lens 616 is configured to redirect the light emitted by the LED 614 to the shared converging lens 608. The shared converging lens 608 is configured to redirect the light from each of the four RLTs 602 into an endoscopic light guide 620. To reduce an overall diameter of the combination of the four RLTs 602, two of the RLTs 602 are arranged on a first plane and the other two of the RLTs 602 are arranged on a second plane offset from the first plane so as to accommodate overlapping of the hemispherical reflectors 612 (shown in FIG. 10) without overlapping of the central collimating lenses 606. The light assembly 600 provides increased light output as a result of the use of 5 total LEDs. The spatial distribution of the four RLTs 602 and the central location of the central LED 604 provides for increased uniformity in the intensity of light transmitted into a light acceptance cone of the light guide 620, thereby increasing uniformity in the distribution of light emitted by the endoscope onto the phonating vocal cords.

Figure 10:
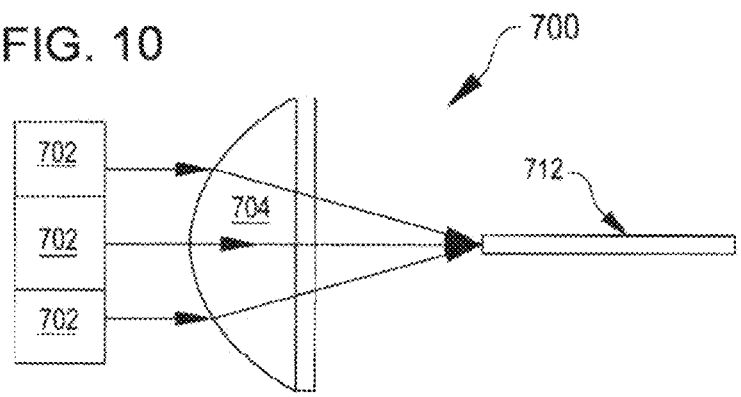
FIGS. 10, 11, and 12 illustrate another embodiment of a stroboscopic light assembly that can be employed in the stroboscopic endoscope system of FIG. 1.
Figure 11:
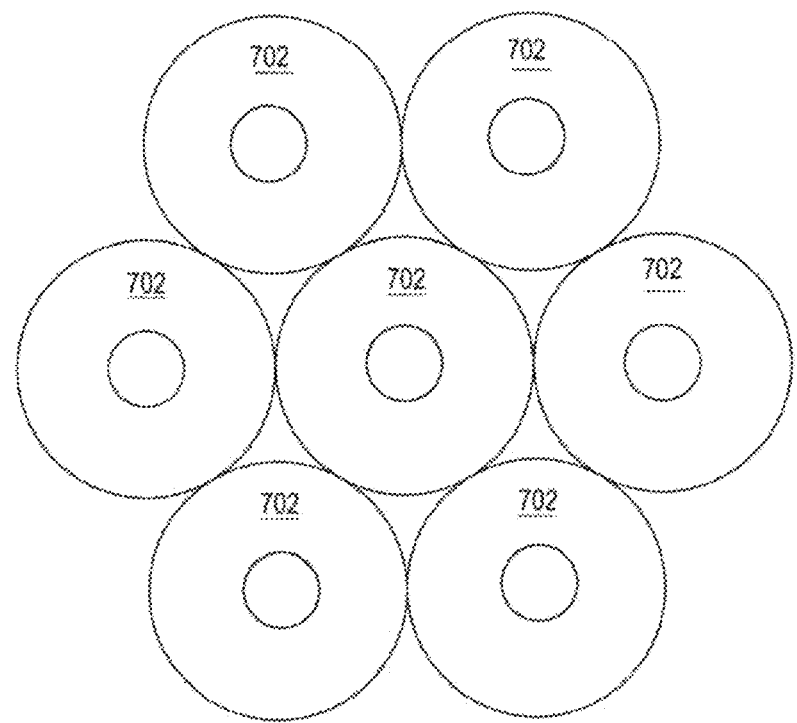
Figure 12:
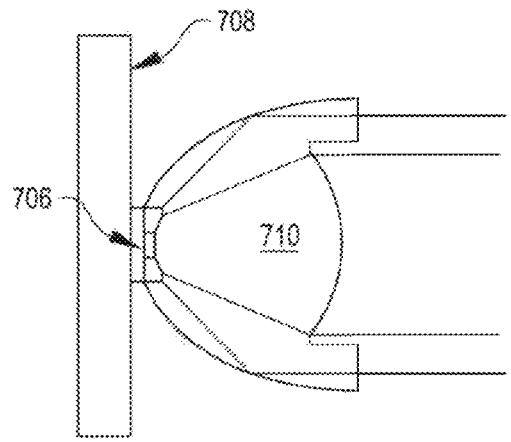

FIGS. 10, 11, and 12 illustrate a stroboscopic light assembly 700 that can be included in the base/illumination unit 26. The light assembly 700 includes seven total internal reflection (TIR) transmitters 702 and a shared converging lens 704. The seven TIR transmitters 702 are arranged in a common plane with a center TIR transmitter 702 surrounded by a hexagonal arrangement of the remaining six TIR transmitters 702. Each of the TIR transmitters 702 include a phosphor coated blue LED 706, a reflective base 708, a TIR optical element 710. The phosphor coated blue LED 706 is mounted to the reflective base 708. The LED 702 is intermittently energized to generate a sequence of white light flashes that is coupled into an endoscope light guide 712. In many embodiments, the reflective base 708 functions as a heat sink to absorb heat generated by the LED 706. In many embodiments, the light assembly 700 includes a thermoelectric cooler and heat exchanger as described herein in any of the light assemblies 100, 200 for precooling the reflective base 708.

The sequence of white light flashes emitted by each of the LEDs 706 is transmitted into the endoscope light scope 712 via the reflective base 708, the TIR optical element 710, and the shared converging lens 704. The reflective base 708 and the TIR optical element 710 are configured to redirect portions of the sequence of white light flashes emitted by the LED 706 that would not otherwise be incident onto the shared converging lens 704 so as to be incident on the lens 704, thereby increasing the amount of light from the sequence of white light flashes emitted by the LED 706 that is coupled into the endoscope 14. The TIR optical element 710 is externally shaped to redirect light emitted by the LED 706 onto the lens 704 via total internal reflection of the light within the TIR optical element 710. The light assembly 700 provides increased light output as a result of the use of 7 total LEDs. The spatial distribution of the seven TIR transmitters 702 provides for increased uniformity in the intensity of light transmitted into a light acceptance cone of the light guide 712, thereby increasing uniformity in the distribution of light emitted by the endoscope onto the phonating vocal cords.

Figure 13:
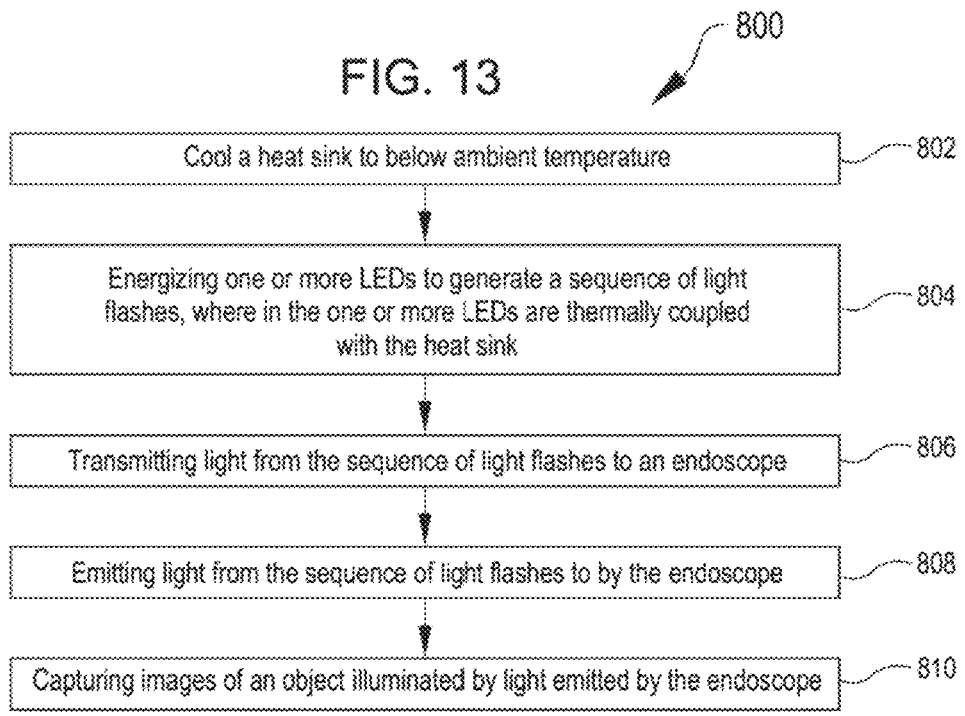
FIG. 13 is a simplified schematic diagram of a method of capturing stroboscopic images that can be employed in the stroboscopic endoscope system of FIG. 1.
Figure 14A:
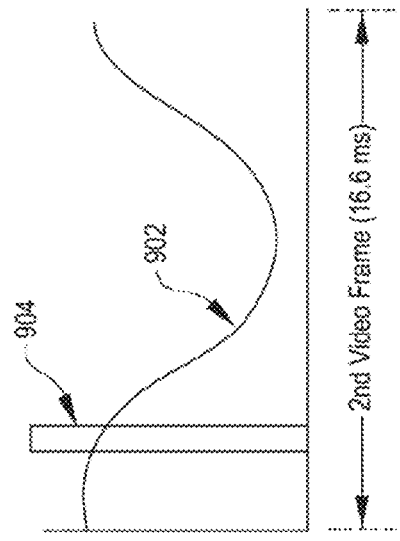
FIGS. 14A through 16D illustrate an approach that can be employed in the stroboscopic endoscope system of FIG. 1 in which multiple illumination light pulses are emitted onto vocal cords of a patient during a video frame to increase the total amount of illumination light.
Figure 14B:
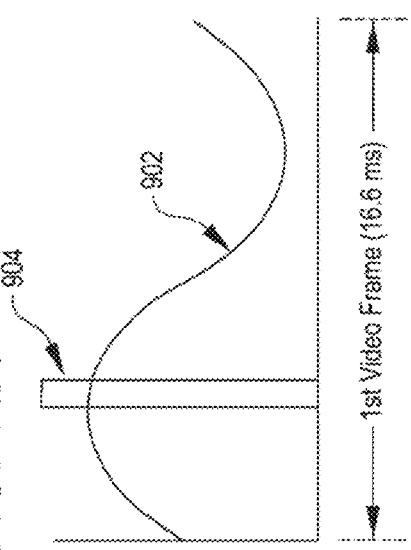
Figure 14C:
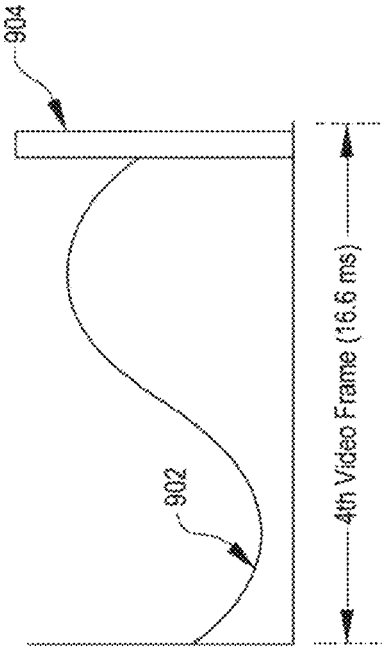
Figure 14D:
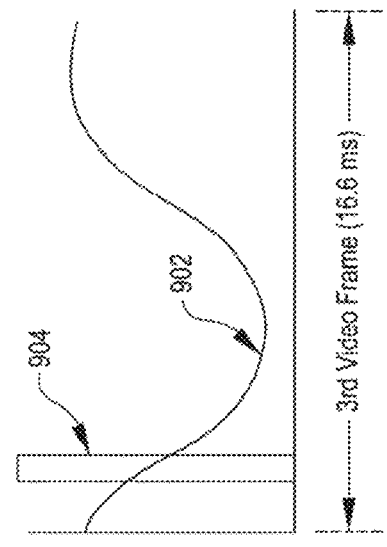
Figure 15A:
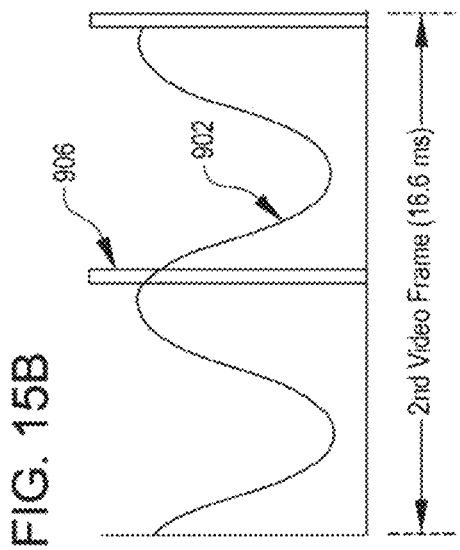
Figure 15B:
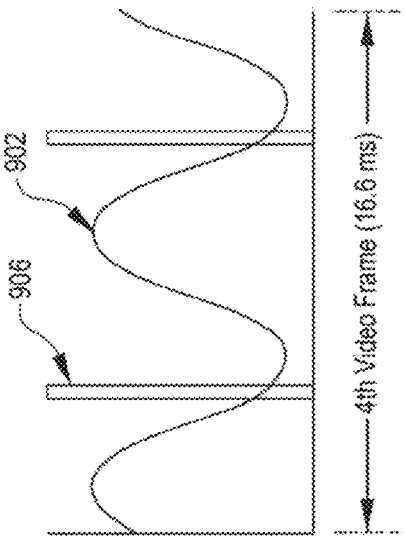
Figure 15C:
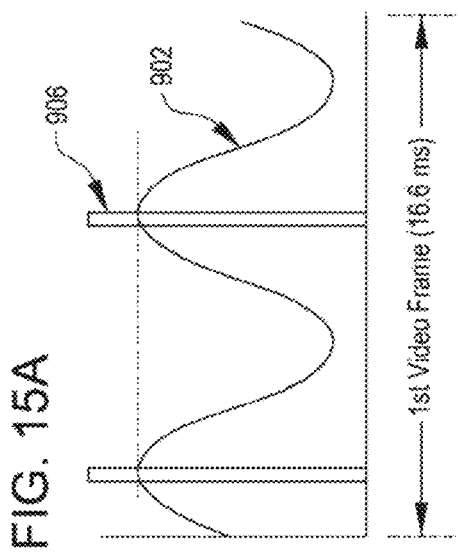
Figure 15D:
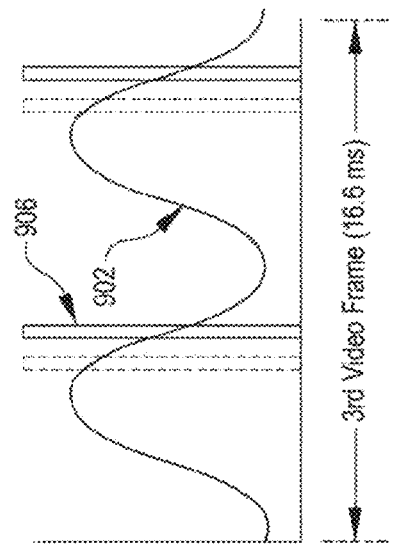
Figure 16A:
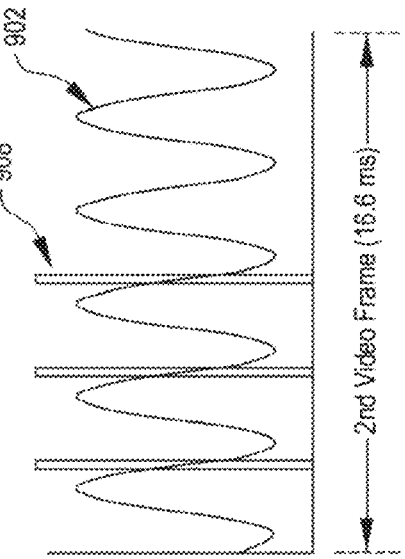
Figure 16B:
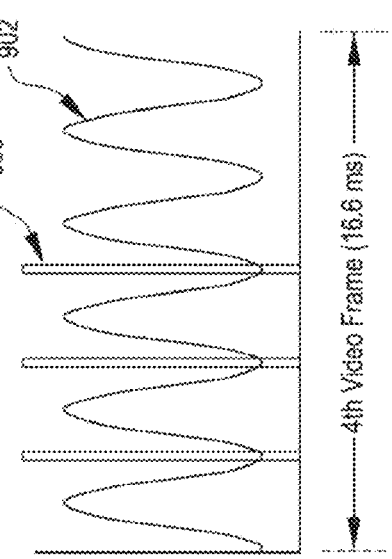
Figure 16C:
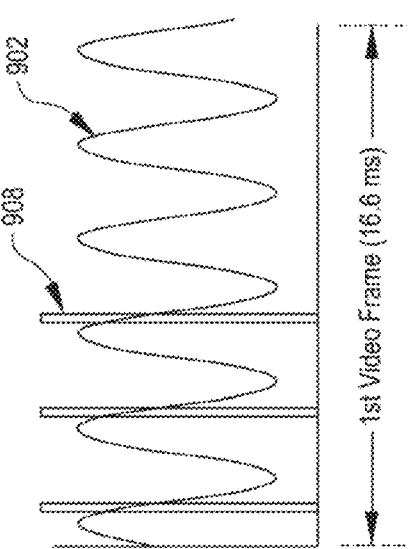
Figure 16D:
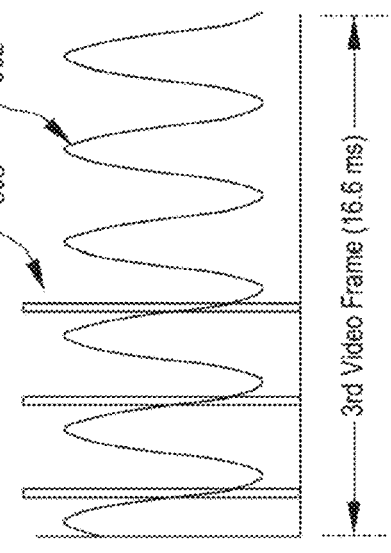

FIG. 13 is a simplified schematic diagram of a method 800 of capturing stroboscopic images, in accordance with embodiments. The method 800 can be accomplished using any suitable stroboscopic imaging system, such as the stroboscopic endoscope system 10 described herein. The method 800 includes acts 802, 804, 806, 808, and 810. In act 802, a heat sink is cooled below an ambient temperature. In act 804, one or more LEDs are energized to generate a sequence of light flashes. The one or more LEDs are thermally coupled with the heat sink so that heat generated by the one or more LEDs is transferred to the heat sink via heat conduction, thereby cooling the one or more LEDs. In many embodiments, the cooling of the one or more LEDs is used to accommodate the use of increased power applied to the one or more LEDs while maintaining an expected service life of the one or more LEDs. In act 806, light from the sequence of light flashes is transmitted to an endoscope. In many embodiments, a light redirecting component (e.g., hemispherical reflector, TIR optical element) is used to increase the amount of light from the sequence of light flashes that is transmitted to the endoscope. In act 808, light from the sequence of light flashes is emitted by the endoscope. In act 810, images are captured of an object (e.g., a phonating larynx) illuminated by the light emitted by the endoscope.

FIGS. 14A through 16D illustrate an approach that can be employed in the stroboscopic endoscope system 10 in which multiple illumination light pulses are emitted onto vocal cords of a patient during each of any suitable and applicable video frame to increase the total amount of illumination light. When a 60 frame/second video frame rate is employed, each video frame has a duration of 16.6 ms. For all patient fundamental phonation frequencies of at least 120 Hz, there are at least two complete cycles of vocal cord displacement phases that occurs during each video frame. For all patient fundamental phonation frequencies less than 120 Hz, there are less than two complete cycles of vocal cord displacement phases that occurs during each video frame.

For example, FIGS. 14A, 14B, 14C, and 14D illustrate four separate video frames selected from a sequence of video frames of video with a 60 frame/second video frame rate and a patient fundamental phonation frequency of 60 Hz, which produces one complete cycle of vocal cord displacement phases per video frame. A trace 902 represents cyclical changes of the vocal cord displacement phases in each of the FIGS. 14A through 16D. When a video frame covers less than two complete cycles of vocal cord displacement phases, a single illumination pulse 904 can be emitted during the video frame to illuminate a phase of the vocal cord displacement for illumination via the video frame. A sequence of video frames can then be used to target a sequence of different phases of the vocal cord displacement via corresponding timing of the respective illumination pulses 904 as illustrated in the four video frames shown. The duration of the single illumination pulse 904 can be limited in duration so as to suitable for use with patient fundamental frequencies up to 120 Hz without resulting in blurring of the image captured in the video frame resulting from the changing of the phase of vocal cord displacement during the single illumination pulse 904. For example, in the illustrated embodiment, the single illumination pulse 904 has a duration of 300 us.

FIGS. 15A, 15B, 15C, and 15D illustrate four separate video frames selected from a sequence of video frames of video with a 60 frame/second video frame rate and a patient fundamental phonation frequency of 120 Hz, which produces two complete cycle of vocal cord displacement phases per video frame. When a video frame covers at least two complete cycles of vocal cord displacement phases, two illumination pulses 906 can be emitted during the video frame to separately illuminate the vocal cords at matching phases of the vocal cord displacement for illumination via the video frame. A sequence of video frames can then be used to target a sequence of different phases of the vocal cord displacement via corresponding timing of the respective sets of the two illumination pulses 906 as illustrated in the four video frames shown. The duration of each of the two illumination pulses 906 can be limited in duration so as to suitable for use with patient fundamental frequencies up to 180 Hz without resulting in blurring of the image captured in the video frame resulting from the changing of the phase of vocal cord displacement during the illumination pulse 906. For example, in the illustrated embodiment, each illumination pulse 906 has a duration of 150 us, which is one-half of the 300 us duration of the single illumination pulse 904, thereby supplying the same total illumination via the two 150 us illumination pulses 906 as for the single 300 us illumination pulse 904.

FIGS. 16A, 16B, 16C, and 16D illustrate four separate video frames selected from a sequence of video frames of video with a 60 frame/second video frame rate and a patient fundamental phonation frequency of 340 Hz, which produces about 5.67 complete cycle of vocal cord displacement phases per video frame. When a video frame covers at least three complete cycles of vocal cord displacement phases, three illumination pulses 908 can be emitted during the video frame to separately illuminate the vocal cords at matching phases of the vocal cord displacement for illumination via the video frame. A sequence of video frames can then be used to target a sequence of different phases of the vocal cord displacement via corresponding timing of the respective sets of the three illumination pulses 908 as illustrated in the four video frames shown. The duration of each of the three illumination pulses 908 can be limited in duration so as to suitable for use without resulting in blurring of the image captured in the video frame resulting from the changing of the phase of vocal cord displacement during the illumination pulse 908. For example, in the illustrated embodiment, each illumination pulse 908 has a duration of 100 us, which is one-third of the 300 us duration of the single illumination pulse 904, thereby supplying the same total illumination via the three 100 us illumination pulses 908 as for the single 300 us illumination pulse 904.

FIG. 17 is a simplified schematic diagram of a method 1000 of setting light pulse durations that can be employed in the approach of FIGS. 14A through 16D. In act 1002, a maximum light pulse duration suitable for use with a maximum phonation frequency that results in less than two complete cycles of vocal cord displacement phases per video frame is determined so to avoid blurring of the image captured in the video frame resulting from the changing of the phase of vocal cord displacement during the single illumination pulse 904. In act 1004, a one-cycle pulse duration can be set to be equal or less than the maximum light pulse duration determined in act 1002. For example, the example single illumination pulse 904 has a 300 us duration. In act 1006, a two-cycle pulse duration can be set to one-half of the one-cycle pulse duration determined in act 1004. In act 1008, a three-cycle pulse duration can be set to one-third of the one-cycle pulse duration determined in act 1004. In act 1010, a four-cycle pulse duration can be set to one-fourth of the one-cycle pulse duration determined in act 1004. A single illumination pulse can be emitted per video frame up to any suitable maximum phonation frequency for which the one-cycle pulse duration is sufficiently short to avoid blurring of the video frame image. Two illumination pulses can be emitted per video frame where the video frame encompasses at least two complete cycles of vocal cord phases up to any suitable maximum phonation frequency for which the two-cycle pulse duration is sufficiently short to avoid blurring of the video frame image. Three illumination pulses can be emitted per video frame where the video frame encompasses at least three complete cycles of vocal cord phases up to any suitable maximum phonation frequency for which the three-cycle pulse duration is sufficiently short to avoid blurring of the video frame image. Four illumination pulses can be emitted per video frame where the video frame encompasses at least four complete cycles of vocal cord phases up to any suitable maximum phonation frequency for which the four-cycle pulse duration is sufficiently short to avoid blurring of the video frame image.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A stroboscopic endoscope system, comprising:
an endoscope comprising a light guide;
a video device configured for imaging vocal chords of a patient that are illuminated via the endoscope;
a first light source;
a light transmission assembly configured to transmit light generated by the first light source into the light guide;
a microphone configured to generate a microphone output signal in response to vocalization of the patient;
a controller operative coupled with the first light source, the video device, and the microphone; wherein the controller is configured to process the microphone output signal to track a fundamental phonation frequency of the patient, wherein the controller is configured to energize the first light source to generate a sequence of two or more light flashes in synchronization with the fundamental phonation frequency during a first video frame of the video device during which the vocal chords complete at least two complete displacement cycles so that the sequence of two or more light flashes illuminate matching segments of the at least two complete displacement cycles;
wherein the sequence of two or more light flashes during the first video frame consists of one of the following:
two light flashes, wherein each of the two light flashes has a duration equal to one-half of a single light flash duration of a single light flash of a different video frame;
three light flashes, wherein each of the three light flashes has a duration equal to one-third of a single light flash duration of a single light flash of a different video frame; or
four light flashes, wherein each of the four light flashes has a duration equal to one-fourth of a single light flash duration of a single light flash of a different video frame.

2. The stroboscopic endoscope system of claim 1, wherein:
the controller is further configured to energize the first light source to generate a single light flash in synchronization with the fundamental phonation frequency during a second video frame of the video device during which the vocal chords complete less than two complete displacement cycles so that the single light flash illuminates a selected segment of one displacement cycle of the less than two complete displacement cycles; and
the single light flash has a single light flash duration.

3. The stroboscopic endoscope system of claim 2, wherein the controller is further configured to energize the first light source to generate a sequence of three or more light flashes in synchronization with the fundamental phonation frequency during a third video frame of the video device during which the vocal chords complete at least three complete displacement cycles so that the sequence of three or more light flashes illuminate matching segments of the at least three complete displacement cycles.

4. The stroboscopic endoscope system of claim 3, wherein the controller is further configured to energize the first light source to generate a sequence of four or more light flashes in synchronization with the fundamental phonation frequency during a fourth video frame of the video device during which the vocal chords complete at least four complete displacement cycles so that the sequence of four or more light flashes illuminate matching segments of the at least four complete displacement cycles.

5. The stroboscopic endoscope system of claim 1, further comprising:
a heat sink coupled with the first light source to transfer heat generated by the first light source to the heat sink; and
a thermoelectric cooler coupled with the heat sink and operable to remove heat from the heat sink,
wherein the controller is operative coupled with the thermoelectric cooler and configured to operate the thermoelectric cooler to cool the heat sink to below an ambient temperature of air surrounding the heat sink prior to energizing the first light source to generate the sequence of light flashes.

6. The stroboscopic endoscope system of claim 5, wherein the heat sink is cooled to at least 5 degrees Celsius below the ambient temperature.

7. The stroboscopic endoscope system of claim 6, wherein the heat sink is cooled to at least 10 degrees Celsius below the ambient temperature.

8. The stroboscopic endoscope system of claim 1, further comprising a hemispherical reflector configured to redirect light generated by the first light source into the light transmission assembly for transmission into the light guide.

9. The stroboscopic endoscope system of claim 8, further comprising an image processor configured to perform color balancing of images captured via the endoscope to compensate for a first shift in spectrum induced by the hemispherical reflector.

10. The stroboscopic endoscope system of claim 9, wherein the first light source comprises a phosphor coating configured to emit white light.

11. The stroboscopic endoscope system of claim 1, further comprising a total internal reflector configured to redirect light generated by the first light source into the light transmission assembly via total internal reflection for transmission into the light guide.

12. The stroboscopic endoscope system of claim 1, wherein:
the first light source is configured to generate monochromatic light;
the light transmission assembly comprises ceramic phosphors; and
the sequence of light flashes excite the ceramic phosphors so as to generate a sequence of white light flashes that are transmitted into the light guide.

13. The stroboscopic endoscope system of claim 12, wherein the ceramic phosphors are excited in a reflective mode.

14. The stroboscopic endoscope system of claim 12, wherein the ceramic phosphors are excited in a transmissive mode.

* * * * *